US012272170B2

(12) United States Patent
Cole et al.

(10) Patent No.: US 12,272,170 B2
(45) Date of Patent: *Apr. 8, 2025

(54) SENSOR AGNOSTIC TEMPERATURE DETECTION SYSTEM

(71) Applicant: The United States of America, as represented by the Secretary of the Navy, Crane, IN (US)

(72) Inventors: Aaron Boyd Cole, Bloomington, IN (US); Marcin Stanislaw Malec, Bloomington, IN (US)

(73) Assignee: The United States of America, Represented by the Secretary of the Navy, Washington, DC (US)

( * ) Notice: Subject to any disclaimer, the term of this patent is extended or adjusted under 35 U.S.C. 154(b) by 849 days.

This patent is subject to a terminal disclaimer.

(21) Appl. No.: 17/358,404

(22) Filed: Jun. 25, 2021

(65) Prior Publication Data

US 2021/0401294 A1 Dec. 30, 2021

Related U.S. Application Data

(60) Provisional application No. 63/044,091, filed on Jun. 25, 2020.

(51) Int. Cl.
*G06V 40/16* (2022.01)
*A61B 5/00* (2006.01)
(Continued)

(52) U.S. Cl.
CPC ............ *G06V 40/161* (2022.01); *A61B 5/015* (2013.01); *A61B 5/1176* (2013.01);
(Continued)

(58) Field of Classification Search
None
See application file for complete search history.

(56) References Cited

U.S. PATENT DOCUMENTS 10,909,835 B1 * 2/2021 Singh .................... G01J 5/53
2018/0180485 A1 * 6/2018 Macmillan ............. H04N 23/23

FOREIGN PATENT DOCUMENTS

EP       3029600 A1 *  6/2016
KR  20180123900 A  * 11/2018

OTHER PUBLICATIONS

English Translation of KR 20180123900 A, Suwon University Industry-Academic Cooperation Foundation, 6 pages, printed May 30, 2024, (Year: 2018).*

* cited by examiner

*Primary Examiner* — Devin B Henson
*Assistant Examiner* — Jennifer Grace Baires-Tweed
(74) *Attorney, Agent, or Firm* — Naval Surface Warfare Center, Crane Division; Patrick B. Law

(57) ABSTRACT

A temperature detection system and method for detecting a correlation between temperatures on a subject and a temperature reference is provided. One or more calibrated temperature reference devices, such as a Body Temperature Reference blackbody system is used with an emissive source detector, such as a Mid Wave Infrared (MWIR) or Long Wave Infrared (LWIR) thermal camera that is capable of imaging both a subject and the calibrated temperature reference devices. A processor maps each pixel within the image to a specific thermal value based on the mean and median reference temperatures from the calibrated temperature reference devices and identifies any pixel in the image having a temperature greater than the reference temperature. This information can be used to detect an elevated temperature from a subject. The system and method can be used to detect fevers, tumors, infections, parasites, and the like.

18 Claims, 4 Drawing Sheets

(51) Int. Cl.
*A61B 5/01* (2006.01)
*A61B 5/1171* (2016.01)
*G06F 18/211* (2023.01)
*G06T 5/70* (2024.01)
*G06T 7/00* (2017.01)
*H04N 5/33* (2023.01)

(52) U.S. Cl.
CPC .......... *A61B 5/7425* (2013.01); *G06F 18/211* (2023.01); *G06T 5/70* (2024.01); *G06T 7/0014* (2013.01); *G06V 40/172* (2022.01); *H04N 5/33* (2013.01); *A61B 2560/0223* (2013.01); *G06T 2207/10048* (2013.01)

SENSOR AGNOSTIC TEMPERATURE DETECTION SYSTEM

CROSS-REFERENCE TO RELATED APPLICATIONS

The present application claims priority to U.S. Provisional Patent Application Ser. No. 63/044,091, filed Jun. 25, 2020, entitled "Sensor Agnostic Febrile Detection System," the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 210071US02) is assigned to the United States Government and is available for licensing for commercial purposes. Licensing and technical inquiries may be directed to the Technology Transfer Office, Naval Surface Warfare Center Crane, email: Cran_CTO@navy.mil.

FIELD OF THE INVENTION

The field of invention relates generally to temperature sensors. More particularly, it pertains to a sensor agnostic temperature detection system for detecting fevers, tumors, infections, parasites, and the like.

BACKGROUND

Fever, also known as pyrexia, is an increase in the body's temperature set point, which causes an elevated temperature. Currently, there is no agreed-upon upper limit for a normal temperature for humans, with ranges between 37.2 and 38.3° C. (99.0 and 100.9° F.) being accepted. A fever is often used as an early indicator of a medical condition. For example, an elevated febrile temperature is a symptom that can be used to diagnose viral, bacterial, and parasitic infections, including influenza, the common cold, meningitis, urinary tract infections, appendicitis, malaria, and most recently, COVID-19.

Current methods for febrile detection include the use of thermometers, such as digital, tympanic, or temporal artery thermometer devices. These devices, however, can only detect temperature for one person at a time, take a relatively long time (up to a few seconds per reading) and are limited in their accuracy, sensitivity, and precision. Additionally, the above-mentioned devices rely on assumptions to determine the temperature of a subject and do not compare the temperature of the subject to a known temperature.

SUMMARY OF THE INVENTION

The present invention relates to a new and improved temperature detection system and method for detecting fevers, tumors, infections, parasites, and the like. One or more calibrated temperature reference devices are used with an emissive source detector, such as a Mid Wave Infrared (MWIR) or Long Wave Infrared (LWIR) thermal camera that is capable of imaging both a subject and the calibrated temperature reference device. A processor maps each pixel within the image to a specific thermal value based on the mean and median reference temperatures from the calibrated temperature reference devices and identifies any pixel in the image having a temperature greater than the reference temperature. This information can be used to detect an elevated temperature from a subject, such as a fever. The inventive device is particularly useful as an early indicator for disease, such as for screening subjects for COVID-19 prior to granting access to a facility.

According to an illustrative embodiment of the present disclosure, it is an object of the invention to compare a subject's temperature to a reference temperature, foregoing the need for calculations and improving accuracy and precision.

According to a further illustrative embodiment of the present disclosure, it is an object of the invention to read temperatures at the frame rate of the imager.

According to a yet another illustrative embodiment of the present disclosure, it is an object of the invention to establish a go/no go or pass/fail test for fever rather than calculating inaccurate temperatures.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Generally, the system is used to detect the surface temperature of a subject in real time (at 0.016 seconds per scan). The temperature information can be used to diagnose viral, bacterial, and parasitic infections, including influenza, the common cold, meningitis, urinary tract infections, appendicitis, malaria, and most recently, COVID-19. Additionally, the system can be used for medical detection of tumors. The system can be adapted for use with humans, animals, and plants. Non-medical uses include oil processing and fuel distillation and chemistry applications where precise temperature measurements are required.

The system includes one or more black body calibrated temperature reference devices, an emissive source detector that captures one or more images, a display, and a processor running temperature detection software, which will be discussed in greater detail below. The system is IA/IT compliant, uses existing hardware, and is system agnostic, allowing for use with any emissive source detection sensor.

Figure 1:
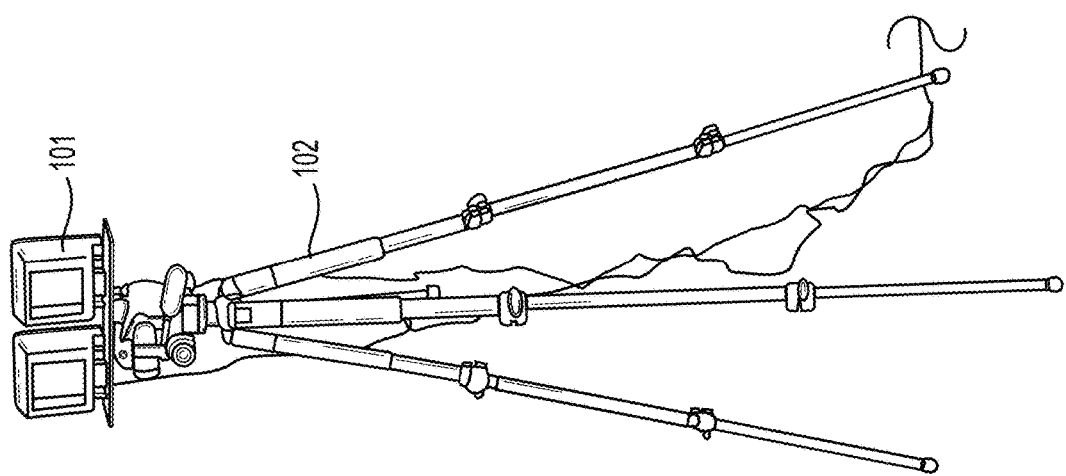
FIG. 1 shows a view of the calibrated temperature reference devices.

Referring now to FIG. 1 there is shown a view of the calibrated temperature reference devices. In a non-limiting example, the reference devices are black body calibrated temperature reference devices, such as one or more Body Temperature Reference (BTR) blackbody systems 101 mounted to a tripod 102. The BTRs 101 provide a stable, uniform, low cost and simple to operate thermal source for human body temperature detection. The BTRs 101 provide a viewable thermal reference area for the emissive source detector that captures one or more images (shown below) to detect the temperature of a subject. A reference source is configured as a set point and is stored into non-volatile memory. After configuration, the BTRs 101 automatically control to the set point upon each power up.

Figure 2:
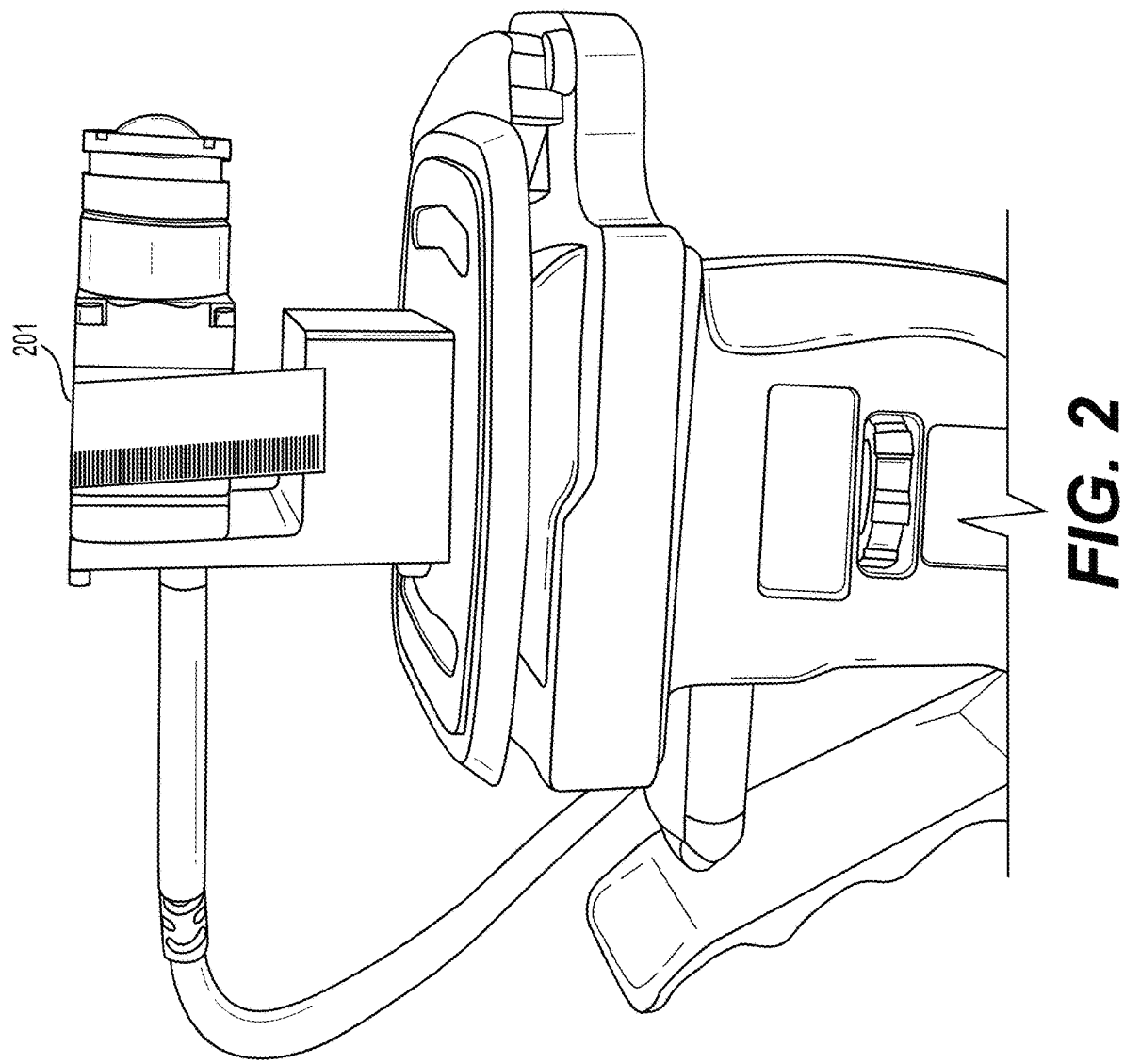
FIG. 2 shows a close-up view of the emissive source detector that captures one or more images.

Referring now to FIG. 2, there is shown a close-up view of the emissive source detector that captures one or more images. The emissive source detector preferably comprises a Mid Wave Infrared (MWIR) or Long Wave Infrared (LWIR) thermal camera 201 (as shown) to perform image capture. These devices generally utilize FLIR infrared video processing architecture to enable advanced image processing and include multiple industry-standard communication interfaces. The LWIR camera 201 provides an infrared or thermal image of a subject and the BTR as discussed above.

Figure 3:
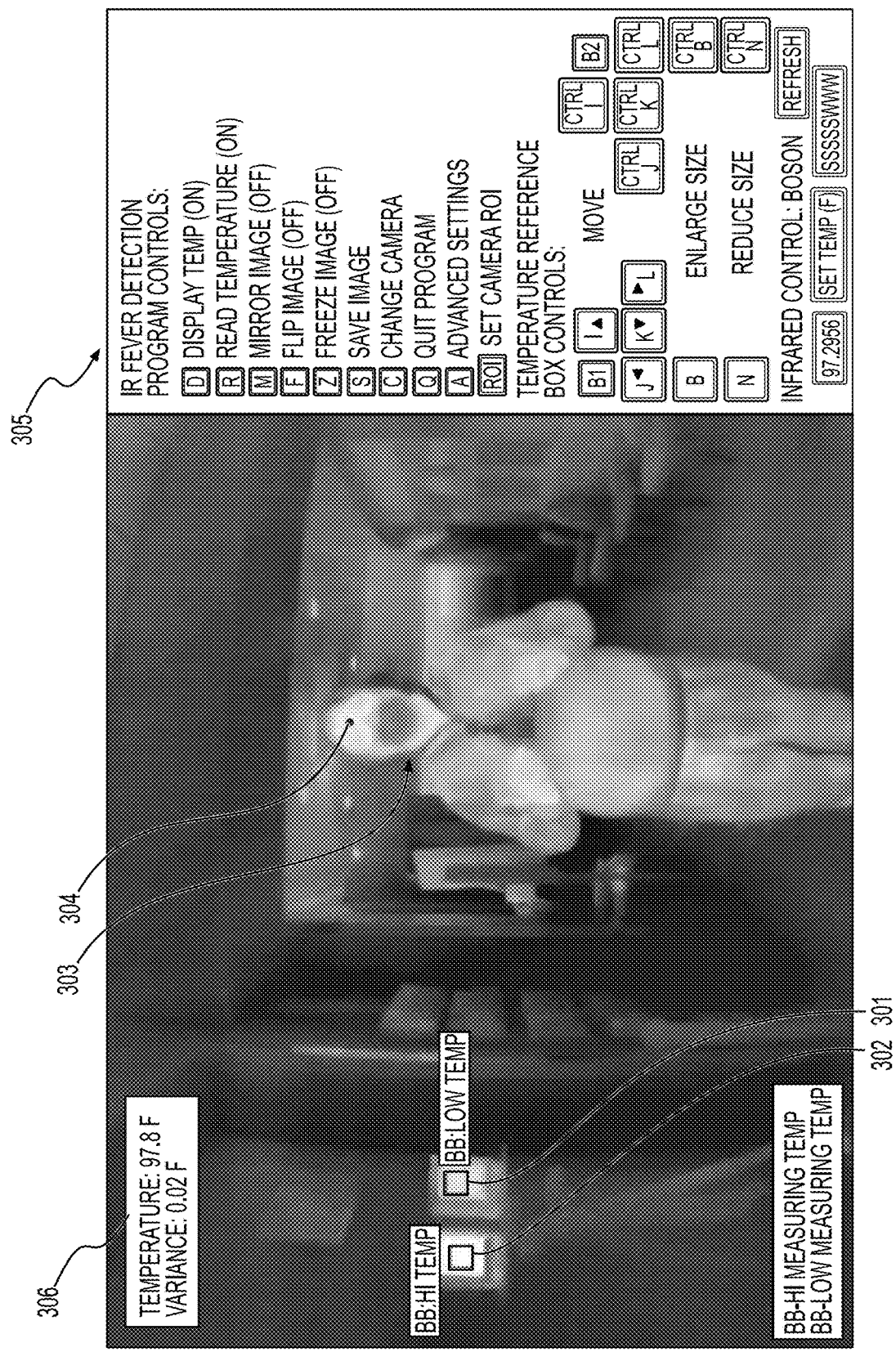
FIG. 3 shows a view of the display image with a subject and the software program controls.

Referring now to FIG. 3, there is shown a view of the display image with a subject and the software program controls. The emissive source detector captures one or more images and provides an infrared image. Two BTRs 301, 302 are present within the image, with the first BTR 301 set at a low temp reference point and the second BTR 302 set at a high temp reference point. Also within the image is a subject 303 (in this case, a human).

The processor, which can be a conventional computer, an electronic tablet, a smartphone, or a similar device, executes instructions read from computer readable memory of the processor in order to receive the one or more images with the subject 303 and the two BTRs 301, 302. The processor then executes instructions to isolate and analyze the pixel values from the two BTRs 301, 302 to find a mean and a median reference temperature. Next, the processor executes instructions to determine that the mean and median reference temperatures are statistically similar, and uses this information to provide a reference temperature. After determining a reference temperature, the processor executes instructions to map each pixel within the image to a specific thermal value based on the mean and median reference temperatures. Any pixel within the image having a temperature greater than the reference temperature is displayed with a color and/or shape, which allows the elevated temperature to be quickly detected by the system or a trained user.

A set of program controls 305 is provided to operate the system. A region of interest of the subject 303 can be easily analyzed by a trained user. As an example, a trained user can scroll over a desired area with a computer mouse, such as the forehead 304, wherein the processor executes instructions to display the temperature 306 of the desired pixels. In the example, the forehead 305 reads a temperature of 98.7 F with a variance of 0.02 F.

Figure 4:
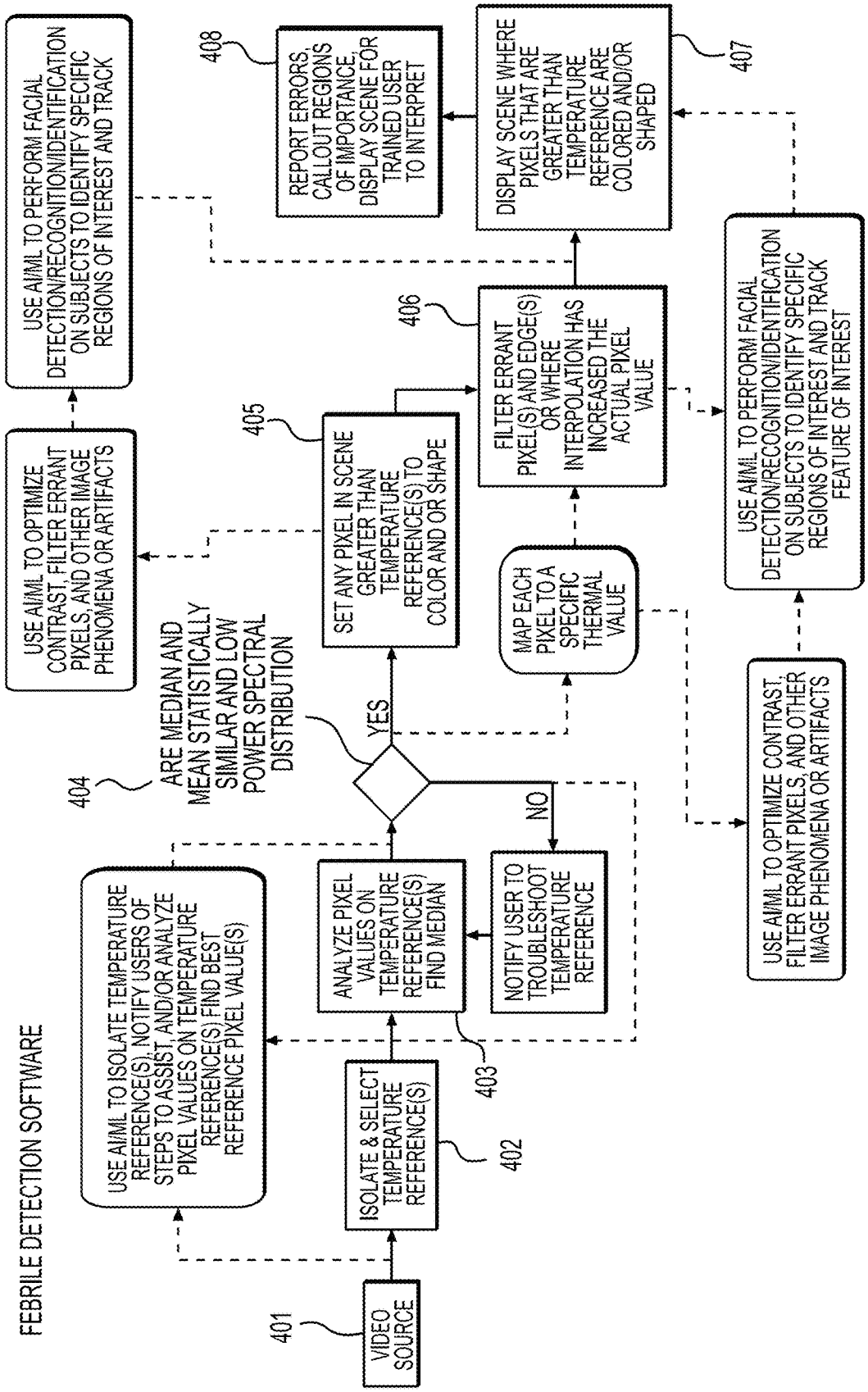
FIG. 4 shows a diagram of the temperature detection software.

FIG. 4 shows a diagram of the temperature detection software. At 401, images from a video source are provided. At 402, temperature references are isolated and selected. At 403, pixel values on the temperature reference are analyzed to find the median. At 404, the median and mean are checked to ensure they are statistically similar. In addition, a low power spectral distribution check is performed. At 405, pixels greater than the temperature reference are set to a specific color and/or shape for ease of identification. At 406, errant pixels on edges or where interpolation has increased the actual pixel value are filtered. At 407, a scene is displayed where pixels that are greater than the reference temperature are shown in the specific color and/or shape. At 408, error reports and callout regions are produced, and the scene is displayed for interpretation by a trained user.

The temperature detection system and method is used to detect a correlation between temperatures on a subject and a temperature reference. The system and method include one or more calibrated temperature reference devices, such as a first and second BTR, an emissive source detector that captures one or more images, such as a LWIR, a display, and a processor in communication with a memory for executing instructions. The processor executes machine readable instructions for performing:

(a) receiving one or more images from the emissive source detector, wherein each image includes a subject and the one or more calibrated temperature reference devices;

(b) isolating the one or more calibrated temperature reference devices within the image and analyzing pixel values of the one or more calibrated temperature reference devices to find a mean and a median reference temperature;

(c) determining that the mean and median reference temperatures are statistically similar, and using the mean and median reference temperatures to provide a reference temperature;

(d) mapping each picture within the image to a specific thermal value based on the mean and median reference temperatures;

(e) identifying any pixel in the image with a temperature greater than the reference temperature and displaying the pixels with a temperature greater than the reference temperature with a color and/or shape.

Additionally, the processor executes machine readable instructions for filtering errant pixels on edges or where interpolation has increased actual pixel value. Additionally, the processor executes machine readable instructions for optimizing contrast and filtering errant pixels, image phenomena, and artifacts. Additionally, the processor executes machine readable instructions for performing facial detection/recognition/identification on the subject to identify and track specific regions of interest. Additionally, the processor executes machine readable instructions for displaying errors. Additionally, the processor executes machine readable instructions for identifying and displaying regions of importance.

The data provides a very precise and accurate correlation between the temperatures on the subject and the temperature reference. The system reads temperatures at the frame rate of the imager, meaning temperatures can be calculated in real time (at 0.016 seconds per scan). Compared to currently existing devices that rely on assumptions to assume what the temperature of the subject is, the inventive system and method directly compare the subject's temperature to a known reference temperature, foregoing the need for calculations and dramatically improving accuracy and precision. The data establish a go/no go or pass/fail test for fever rather than wasting time on calculating inaccurate temperatures. The inventive system can scan all subjects who fit within the field of view of the sensor simultaneously in real time.

The inventive system and method preferably utilize military sensors, which are by design and legislation much more accurate and robust than medical standoff systems. Military Sensors are more adept at detecting very small temperature differences with greater precision and accuracy when compared to consumer off-the-shelf solutions. The inventive system and method are sensor agnostic and can be used with any emissive source detection sensor, such as with MWIR AND LWIR. The inventive system can detect any elevated temperature on a human body, which can be used to call attention to other infections or other medical conditions. The inventive system can track, observe, and scan moving subjects from 0 to beyond 600 feet without interference. Additionally, the inventive system can function outdoors as long as the temperature reference and the subject are not in direct sunlight.

Although the invention has been described in detail with reference to certain preferred embodiments, variations and modifications exist within the spirit and scope of the invention as described and defined in the following claims.

The invention claimed is:

1. A temperature detection system for detecting a correlation between temperatures on a subject and a reference temperature, said system comprising:
   one or more calibrated temperature reference devices;
   an emissive source detector that captures one or more images;
   a display; and
   a processor in communication with a memory, said processor executing machine readable instructions for performing:
   (a) receiving the one or more images from said emissive source detector, wherein at least one of the one or more images includes the subject and said one or more calibrated temperature reference devices;
   (b) isolating said one or more calibrated temperature reference devices within the at least one of the one or more images and analyzing pixel values of said one or more calibrated temperature reference devices to find a mean reference temperature and a median reference temperature;
   (c) comparing the mean reference temperature with the median reference temperature to determine when the median and mean reference temperatures are statistically similar, and using said mean and median reference temperatures to determine the reference temperature when the median and mean reference temperatures are statistically similar;
   (d) mapping each pixel within the at least one of the one or more images to a specific thermal value based on said mean and median reference temperatures; and
   (e) identifying any pixel in the least one of the one or more images with a temperature greater than said reference temperature and displaying said identified pixels on the display with a temperature greater than said reference temperature with a color and/or shape.

2. The system of claim 1, further comprising the processor executing machine readable instructions for further performing:
   filtering errant pixels in the at least one of the one or more images on edges or where interpolation has increased actual pixel value prior to displaying the identified pixels on the display.

3. The system of claim 1, further comprising the processor executing machine readable instructions for further performing:
   optimizing contrast and filtering errant pixels, image phenomena, and artifacts in the at least one of the one or more images prior to displaying the identified pixels on the display.

4. The system of claim 1, further comprising the processor executing machine readable instructions for further performing:
   performing facial detection/recognition/identification on said subject to identify and track specific regions of interest in the at least one of the one or more images prior to displaying the identified pixels on the display.

5. The system of claim 1, further comprising the processor executing machine readable instructions for further performing:
   displaying errors in the at least one of the one or more images as part of displaying the identified pixels on the display.

6. The system of claim 1, further comprising the processor executing machine readable instructions for further performing:
   identifying and displaying regions of importance in the at least one of the one or more images as part of displaying the identified pixels on the display.

7. A method for detecting a correlation between temperatures on a subject and a reference temperature comprising:
   (a) receiving one or more images from an emissive source detector, wherein at least one of the one or more images includes the subject and one or more calibrated temperature reference devices;
   (b) isolating said one or more calibrated temperature reference devices within the at least one of the one or more images and analyzing pixel values of said one or more calibrated temperature reference devices to find a mean reference temperature and a median reference temperature;
   (c) comparing the mean reference temperature with the median reference temperature to determine when the median and mean reference temperatures are statistically similar, and using said mean and median reference temperatures to determine the reference temperature when the median and mean reference temperatures are statistically similar;
   (d) mapping each pixel within the at least one of the one or more images to a specific thermal value based on said mean and median reference temperatures; and
   (e) identifying any pixel in the least one of the one or more images with a temperature greater than said reference temperature and displaying said identified pixels on a display with a temperature greater than said reference temperature with a color and/or shape.

8. The method of claim 7, further comprising:
   filtering errant pixels in the at least one of the one or more images on edges or where interpolation has increased actual pixel value prior to displaying the identified pixels on the display.

9. The method of claim 7, further comprising:
   optimizing contrast and filtering errant pixels, image phenomena, and artifacts in the at least one of the one or more images prior to displaying the identified pixels on the display.

10. The method of claim 7, further comprising:
    performing facial detection/recognition/identification on said subject to identify and track specific regions of interest in the at least one of the one or more images prior to displaying the identified pixels on the display.

11. The method of claim 7, further comprising:
    displaying errors in the at least one of the one or more images as part of displaying the identified pixels on the display.

12. The method of claim 7, further comprising:
    identifying and displaying regions of importance in the least one of the one or more images as part of displaying the identified pixels on the display.

13. A method for detecting a correlation between temperatures on a subject and a reference temperature, said method comprising:

(a) receiving one or more images from an emissive source detector, wherein at least one of the one or more images includes the subject and said one or more calibrated temperature reference devices;
(b) executing instructions read from a computer readable memory with a processor to isolate said one or more calibrated temperature reference devices within the at least one of the one or more images and analyze pixel values of said one or more calibrated temperature reference devices to find a mean reference temperature and a median reference temperature;
(c) executing instructions read from said computer readable memory with said processor to compare the mean reference temperature with the median reference temperature to determine when the median and mean reference temperatures are statistically similar, and use said mean and median reference temperatures to determine the reference temperature when the median and mean reference temperatures are statistically similar;
(d) executing instructions read from said computer readable memory with said processor to map each pixel within the at least one of the one or more images to a specific thermal value based on said mean and median reference temperatures; and
(e) executing instructions read from said computer readable memory with said processor to identify any pixel in the least one of the one or more images with a temperature greater than said reference temperature and display said identified pixels on a display with a temperature greater than said reference temperature with a color and/or shape.

14. The method of claim 13, further comprising:
executing instructions read from said computer readable memory with said processor to filter errant pixels in the least one of the one or more images on edges or where interpolation has increased actual pixel value prior to displaying the identified pixels on the display.

15. The method of claim 13, further comprising:
executing instructions read from said computer readable memory with said processor to optimize contrast and filter errant pixels, image phenomena, and artifacts in the least one of the one or more images prior to displaying the identified pixels on the display.

16. The method of claim 13, further comprising:
executing instructions read from said computer readable memory with said processor to perform facial detection/recognition/identification on said subject to identify and track specific regions of interest in the least one of the one or more images prior to displaying the identified pixels on the display.

17. The method of claim 13, further comprising:
executing instructions read from said computer readable memory with said processor to display errors in the at least one of the one or more images as part of displaying the identified pixels on the display.

18. The method of claim 13, further comprising:
executing instructions read from said computer readable memory with said processor to identify and display regions of importance in the at least one of the one or more images as part of displaying the identified pixels on the display.

* * * * *